(12) United States Patent
Chan et al.

(10) Patent No.: US 7,122,350 B2
(45) Date of Patent: Oct. 17, 2006

(54) METHODS FOR ENHANCING EXPRESSION OF RECOMBINANT PROTEINS

(75) Inventors: Chung Chan, Sammamish, WA (US); Tracey A. Pownder, Bellevue, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 11/054,063

(22) Filed: Feb. 9, 2005

(65) Prior Publication Data

US 2005/0164349 A1 Jul. 28, 2005

Related U.S. Application Data

(63) Continuation-in-part of application No. 11/008,853, filed on Dec. 10, 2004.

(60) Provisional application No. 60/529,412, filed on Dec. 12, 2003.

(51) Int. Cl.
*C12P 21/06* (2006.01)
*C12N 15/00* (2006.01)
*C12N 1/20* (2006.01)

(52) U.S. Cl. .................. 435/69.1; 435/252.3; 435/320

(58) Field of Classification Search ............... 435/69.1, 435/320.1; 536/23.1
See application file for complete search history.

(56) References Cited

U.S. PATENT DOCUMENTS 5,545,541 A * 8/1996 Molin et al. ................. 435/480
6,271,359 B1 * 8/2001 Norris et al. .............. 536/23.1

OTHER PUBLICATIONS

Estrem et al., "Identification of an UP element consensus sequnece for bacterial promoters," Proc. Natl. Acad. Sci. USA (Aug. 18, 1998), 95(17), p. 9761-6.*

* cited by examiner

*Primary Examiner*—Maryam Monshipouri
*Assistant Examiner*—Agnes Rooke
(74) *Attorney, Agent, or Firm*—Shelby J. Walker

(57) ABSTRACT

The present invention provides two novel *E. coli* synthetic promoters, Syn 1 and Syn 2. Syn 1 and Syn 2 are two tight regulated synthetic promoters that control uninduced, leaky expression of proteins that are toxic and interfere with production of recombinant protein from an *E. coli* expression system.

10 Claims, No Drawings

SEQUENCE LISTING

```
<160> NUMBER OF SEQ ID NOS: 29

<210> SEQ ID NO 1
<211> LENGTH: 101
<212> TYPE: DNA
<213> ORGANISM: Artificial Sequence
<220> FEATURE:
<223> OTHER INFORMATION: Syn 1 promoter

<400> SEQUENCE: 1
agctgttgac attgtgagcg gataacaata taatgtgtgg aattgtgagc ggataacaat        60
ttcacacaga attcattaaa gaggagaaat taactcccgg g                           101

<210> SEQ ID NO 2
<211> LENGTH: 141
<212> TYPE: DNA
<213> ORGANISM: Artificial Sequence
<220> FEATURE:
<223> OTHER INFORMATION: Syn 2 promoter

<400> SEQUENCE: 2
gcgccgacat cataacggtt ctggaaaatt attttaaatt tcctcttgac attgtgagcg        60
gataacaata taatgtgtgg aattgtgagc ggataacaat ttcacacaga attcattaaa       120
gaggagaaat taactcccgg g                                                 141

<210> SEQ ID NO 3
<211> LENGTH: 50
<212> TYPE: DNA
<213> ORGANISM: Artificial Sequence
<220> FEATURE:
<223> OTHER INFORMATION: oligonucleotide primer zc29,740

<400> SEQUENCE: 3
ttgacaatta atcatcggct cgtataatgt gtggaattgt gagcggataa                    50

<210> SEQ ID NO 4
```

```
<211> LENGTH: 42
<212> TYPE: DNA
<213> ORGANISM: Artificial Sequence
<220> FEATURE:
<223> OTHER INFORMATION: oligonucleotide primer zc29,741

<400> SEQUENCE: 4
tctgatttaa tctgtatcag gctgaaaatc ttatctcatc cg                        42

<210> SEQ ID NO 5
<211> LENGTH: 62
<212> TYPE: DNA
<213> ORGANISM: Artificial Sequence
<220> FEATURE:
<223> OTHER INFORMATION: oligonucleotide primer zc29,736

<400> SEQUENCE: 5
gtggaattgt gagcggataa caatttcaca cagaattcat aaagaggag aaattaactc      60 cc                                                                    62

<210> SEQ ID NO 6
<211> LENGTH: 63
<212> TYPE: DNA
<213> ORGANISM: Artificial Sequence
<220> FEATURE:
<223> OTHER INFORMATION: oligonucleotide primer zc29,738

<400> SEQUENCE: 6
gctgaaaatc ttatctcatc cgccaaaaca cccgggagtt aatttctcct ctttaatgaa    60
ttc                                                                   63

<210> SEQ ID NO 7
<211> LENGTH: 50
<212> TYPE: DNA
<213> ORGANISM: Artificial Sequence
<220> FEATURE:
<223> OTHER INFORMATION: oligonucleotide primer zc42,180

<400> SEQUENCE: 7
gcgccgacat cataacggtt ctggcaaata ttctgaaatg agctgttgac                50

<210> SEQ ID NO 8
<211> LENGTH: 43
<212> TYPE: DNA
<213> ORGANISM: Artificial Sequence
<220> FEATURE:
<223> OTHER INFORMATION: oligonucleotide primer zc42,167

<400> SEQUENCE: 8
cgccaaaaca cccgggagtt aatttctcct ctttaatgaa ttc                       43

<210> SEQ ID NO 9
<211> LENGTH: 63
<212> TYPE: DNA
<213> ORGANISM: Artificial Sequence
<220> FEATURE:
<223> OTHER INFORMATION: oligonucleotide primer zc42,181

<400> SEQUENCE: 9
ttctcctctt taatgaattc tgtgtgaaat tgttatccgc tcacaattcc acacattata    60
ttg                                                                   63

<210> SEQ ID NO 10
<211> LENGTH: 60
```

```
<212> TYPE: DNA
<213> ORGANISM: Artificial Sequence
<220> FEATURE:
<223> OTHER INFORMATION: oligonucleotide primer zc42,179

<400> SEQUENCE: 10
ttctgaaatg agctgttgac attgtgagcg gataacaata taatgtgtgg aattgtgagc      60

<210> SEQ ID NO 11
<211> LENGTH: 44
<212> TYPE: DNA
<213> ORGANISM: Artificial Sequence
<220> FEATURE:
<223> OTHER INFORMATION: oligonucleotide primer zc42,734

<400> SEQUENCE: 11
cgttctggat aatgtttttt gcgccgacat cataacggtt ctgg                      44

<210> SEQ ID NO 12
<211> LENGTH: 51
<212> TYPE: DNA
<213> ORGANISM: Artificial Sequence
<220> FEATURE:
<223> OTHER INFORMATION: oligonucleotide primer zc42,733

<400> SEQUENCE: 12
cgccaaaaca cccgggagtt aatttctcct ctttaatgaa ttctgtgtga a               51

<210> SEQ ID NO 13
<211> LENGTH: 66
<212> TYPE: DNA
<213> ORGANISM: Artificial Sequence
<220> FEATURE:
<223> OTHER INFORMATION: oligonucleotide primer zc42,721

<400> SEQUENCE: 13
cgacatcata acggttctgg aaaattattt taaatttcct cttgacattg tgagcggata     60
acaata                                                                66

<210> SEQ ID NO 14
<211> LENGTH: 73
<212> TYPE: DNA
<213> ORGANISM: Artificial Sequence
<220> FEATURE:
<223> OTHER INFORMATION: oligonucleotide primer zc42,718

<400> SEQUENCE: 14
tttaatgaat tctgtgtgaa attgttatcc gctcacaatt ccacacatta tattgttatc     60
cgctcacaat gtc                                                        73

<210> SEQ ID NO 15
<211> LENGTH: 66
<212> TYPE: DNA
<213> ORGANISM: Artificial Sequence
<220> FEATURE:
<223> OTHER INFORMATION: oligonucleotide primer zc42,719

<400> SEQUENCE: 15
cgacatcata acggttctgg aaaaattttt taaaaaaata cttgacattg tgagcggata     60
acaata                                                                66

<210> SEQ ID NO 16
<211> LENGTH: 66
<212> TYPE: DNA
```

<210> SEQ ID NO 17
<211> LENGTH: 66
<212> TYPE: DNA
<213> ORGANISM: Artificial Sequence
<220> FEATURE:
<223> OTHER INFORMATION: oligonucleotide primer zc42,720

<400> SEQUENCE: 16

```
cgacatcata acggttctgg aaaaaaagat caaaaaaata cttgacattg tgagcggata      60
acaata                                                                66
```

<210> SEQ ID NO 17
<211> LENGTH: 66
<212> TYPE: DNA
<213> ORGANISM: Artificial Sequence
<220> FEATURE:
<223> OTHER INFORMATION: oligonucleotide primer zc42,727

<400> SEQUENCE: 17

```
cgacatcata acggttctgg agagaaagca aaataaatg  cttgacattg tgagcggata      60
acaata                                                                66
```

<210> SEQ ID NO 18
<211> LENGTH: 462
<212> TYPE: DNA
<213> ORGANISM: Homo sapiens

<400> SEQUENCE: 18

```
atgctgaaaa ccctgaacct gggtagctgt gtgatcgcca ccaacctgca ggaaatccgt      60
aacggttct  ctgagatccg tggcagcgtg caggccaaag atggtaacat tgacatccgt     120
atcctgcgtc gtaccgagtc tctgcaggac accaaaccgg cgaaccgttg ctgcctgctg     180
cgccacctgc tgcgtctgta tctggaccgt gttttcaaaa actaccagac cccggaccac     240
tataccctgc gtaaaatcag cagcctggcc aactccttcc tgaccatcaa aaaagacctg     300
cgtctgtgtc acgcccacat gacctgccac tgtggtgagg aagcaatgaa aaatacagc      360
cagattctga gccacttcga aaaactggaa ccgcaggcag cagtggtgaa agctctgggt     420
gaactggaca ttctgctgca gtggatggag gagaccgaat ag                        462
```

<210> SEQ ID NO 19
<211> LENGTH: 153
<212> TYPE: PRT
<213> ORGANISM: Homo sapiens

<400> SEQUENCE: 19

```
Met Leu Lys Thr Leu Asn Leu Gly Ser Cys Val Ile Ala Thr Asn Leu
 1               5                  10                  15

Gln Glu Ile Arg Asn Gly Phe Ser Glu Ile Arg Gly Ser Val Gln Ala
            20                  25                  30

Lys Asp Gly Asn Ile Asp Ile Arg Ile Leu Arg Arg Thr Glu Ser Leu
        35                  40                  45

Gln Asp Thr Lys Pro Ala Asn Arg Cys Cys Leu Leu Arg His Leu Leu
    50                  55                  60

Arg Leu Tyr Leu Asp Arg Val Phe Lys Asn Tyr Gln Thr Pro Asp His
65                  70                  75                  80

Tyr Thr Leu Arg Lys Ile Ser Ser Leu Ala Asn Ser Phe Leu Thr Ile
                85                  90                  95

Lys Lys Asp Leu Arg Leu Cys His Ala His Met Thr Cys His Cys Gly
            100                 105                 110

Glu Glu Ala Met Lys Lys Tyr Ser Gln Ile Leu Ser His Phe Glu Lys
        115                 120                 125
```

-continued

Leu Glu Pro Gln Ala Ala Val Val Lys Ala Leu Gly Glu Leu Asp Ile
    130                 135                 140

Leu Leu Gln Trp Met Glu Glu Thr Glu
145                 150

<210> SEQ ID NO 20
<211> LENGTH: 66
<212> TYPE: DNA
<213> ORGANISM: Artificial Sequence
<220> FEATURE:
<223> OTHER INFORMATION: oligonucleotide primer zc29,957

<400> SEQUENCE: 20
caatttcaca cagaattcat taaagaggag aaattaacta tgctgaaaac cctgaacctg    60
ggtagc    66

<210> SEQ ID NO 21
<211> LENGTH: 38
<212> TYPE: DNA
<213> ORGANISM: Artificial Sequence
<220> FEATURE:
<223> OTHER INFORMATION: oligonucleotide primer zc23,993

<400> SEQUENCE: 21
gtatcaggct gaaaatctta tctcatccgc caaaacac    38

<210> SEQ ID NO 22
<211> LENGTH: 64
<212> TYPE: DNA
<213> ORGANISM: Artificial Sequence
<220> FEATURE:
<223> OTHER INFORMATION: oligonucleotide primer zc47,073

<400> SEQUENCE: 22
acaatttcac acagaattca ttaaagagga gaaattaact atgaggggca tgaagctgct    60
gggg    64

<210> SEQ ID NO 23
<211> LENGTH: 64
<212> TYPE: DNA
<213> ORGANISM: Artificial Sequence
<220> FEATURE:
<223> OTHER INFORMATION: oligonucleotide primer zc47,074

<400> SEQUENCE: 23
tctgtatcag gctgaaaatc ttatctcatc cgccaaaaca tcacttcagc atcacctcca    60
ctgg    64

<210> SEQ ID NO 24
<211> LENGTH: 17
<212> TYPE: DNA
<213> ORGANISM: Artificial Sequence
<220> FEATURE:
<223> OTHER INFORMATION: UP element consensus sequence

<400> SEQUENCE: 24
aaaaattttt taaaaaa    17

<210> SEQ ID NO 25
<211> LENGTH: 17
<212> TYPE: DNA
<213> ORGANISM: Artificial Sequence
<220> FEATURE:

<223> OTHER INFORMATION: rrnDP1 UP element

<400> SEQUENCE: 25
aaaaaaagat caaaaaa                                                    17

<210> SEQ ID NO 26
<211> LENGTH: 18
<212> TYPE: DNA
<213> ORGANISM: Artificial Sequence
<220> FEATURE:
<223> OTHER INFORMATION: rrnBP2 UP element

<400> SEQUENCE: 26
gagagaaagc aaaaataa                                                   18

<210> SEQ ID NO 27
<211> LENGTH: 64
<212> TYPE: DNA
<213> ORGANISM: Artificial Sequence
<220> FEATURE:
<223> OTHER INFORMATION: oligonucleotide primer zc48069

<400> SEQUENCE: 27
acaatttcac acagaattca ttaaagagga gaaattaact atgaacatta ccgacatcat     60
gaac                                                                  64

<210> SEQ ID NO 28
<211> LENGTH: 67
<212> TYPE: DNA
<213> ORGANISM: Artificial Sequence
<220> FEATURE:
<223> OTHER INFORMATION: oligonucleotide primer zc48070

<400> SEQUENCE: 28
tctgtatcag gctgaaaatc ttatctcatc cgccaaaaca tcagcccatt aacattgcgt     60
caagttg                                                               67

<210> SEQ ID NO 29
<211> LENGTH: 1080
<212> TYPE: DNA
<213> ORGANISM: Bacteriophage T7 0.7 virus

<400> SEQUENCE: 29
atgaacatta ccgacatcat gaacgctatc gacgcaatca agcactgcc aatctgtgaa      60 cttgacaagc gtcaaggtat gcttatcgac ttactggtcg agatggtcaa cagcgagacg    120
tgtgatggcg agctaaccga actaaatcag gcacttgagc atcaagattg gtggactacc    180
ttgaagtgtc tcacggctga cgcagggttc aagatgctcg gtaatggtca cttctcggct    240
gcttatagtc acccgctgct acctaacaga gtgattaagg tgggctttaa gaaagaggat    300
tcaggcgcag cctataccgc attctgccgc atgtatcagg tcgtcctgg tatccctaac     360 gtctacgatg tacagcgcca cgctggatgc tatacggtgg tacttgacgc acttaaggat    420
tgcgagcgtt tcaacaatga tgcccattat aaatacgctg agattgcaag cgacatcatt    480
gattgcaatt cggatgagca tgatgagtta actggatggg atggtgagtt tgttgaaact    540
tgtaaactaa tccgcaagtt ctttgagggc atcgcctcat cgacatgca tagcgggaac    600 atcatgttct caaatggaga cgtaccatac atcaccgacc cggtatcatt ctcgcagaag    660
aaagacggtg gcgcattcag catcgaccct gaggaactca tcaaggaagt cgaggaagtc    720
gcacgacaga agaaattga ccgcgctaag gcccgtaaag aacgtcacga ggggcgctta    780

```
gaggcacgca gattcaaacg tcgcaaccgc aaggcacgta aagcacacaa agctaagcgc    840
gaaagaatgc ttgctgcgtg gcgatgggct gaacgtcaag aacggcgtaa ccatgaggta    900
gctgtagatg tactaggaag aaccaataac gctatgctct gggtcaacat gttctctggg    960
gactttaagg cgcttgagga acgaatcgcg ctgcactggc gtaatgctga ccggatggct   1020
atcgctaatg gtcttacgct caacattgat aagcaacttg acgcaatgtt aatgggctga   1080
```

METHODS FOR ENHANCING EXPRESSION OF RECOMBINANT PROTEINS

This application is a continuation-in-part of U.S. application Ser. No. 11/008,853, filed Dec. 10, 2004, which claims the benefit of U.S. Provisional Application Ser. No. 60/529,412, filed Dec. 12, 2003, both of which are herein incorporated by reference.

BACKGROUND OF THE INVENTION

The increased availability and identification of genes from human and other genomes has led to an increased need for efficient expression of recombinant proteins. The expression of proteins in bacteria is by far the most widely used approach for the production of cloned genes. For many reasons, expression in bacteria is preferred to expression in eukazyotic cells. For example, bacteria are much easier to grow than eukaryozic cells. More specifically, the availability of a wealth of sophisticated molecular genetic tools and thousands of mutants make $E.$ $coil$, as an expression host, extremely useful for protein production. However, the high-level production of functional proteins in $E.$ $coli.$, especially those from eukaryotic sources has often been difficult. Inefficient translation initiation is the most common reason for poor expression. See e.g. Schoner et. al., $Methods$ $Enzymol.$ 185:94–103 (1990).

Initiation sites where the enzyme binds to specific nucleouides sequences are known as promoters. By determining the nucleotide sequences of protected regions from numerous $E.$ $coli$ genes, a consensus sequence for the $E.$ $coli$ promoter has been identified. The most conserved sequence is a hexamer (–10 element) centered at about the –10 position from the transcription initiation site. The consensus sequence is TATAAT. Upstream sequences around –35 also have a region of sequence similarity, TTGACA (–35 element), which is most evident in efficient promoters. The distance separating the –35 and –10 elements is between 16 and 18 base pairs in 90% of promoters. The distance is critical for maintaining necessary structural conformation of the two sites for RNA polymerase binding.

Regulation of promoter regions in prokaryotic genes contain multiple binding sites for transcription factors. Interactions between and among regulatory proteins bound to promoter regions produce both positive and negative synergistic effects on gene expression. Regulation of lac operon of $E.$ $coli$ has been studied extensively and has become a model for negative control of gene expression at the level of transcription. (See, e.g., Muller-Hill B., $Prog$ $Biophys$ $Mol.$ $Biol.,$ 30(2–3): 227–52, 1975; and Sauer R T, $Structure$ 4(3): 219–22, 1996.) Transcription of the lac operon in $Escherichia$ $coli$ is repressed by the binding of Lac repressor (LacR) to lac operator O1, a pseudo-palindromic sequence centered 11 base pairs downstream of the transcription start. Repressors appear to inhibit transcription by either steric hindrance preventing the binding of DNA polymerase to the promoter, or by preventing the transition of the closed state of the promoter to the open state. The lac repressor exists as a tetramer, and full repression of the wild-type lac promoter by wild-type LacR requires the presence of at least two other operator sequences that must not only be in close proximity to the lac operator O1, i.e. located at base pair 401 and 92 for the auxiliary operators O2 and O3, respectively, but the operator sequences must also be present on the same side of the DNA helix. LacR mutants lacking the C-terminal heptad repeat are only capable of dimer formation, yet still repress, albeit at a much reduced level. Repression of the lac promoter by the mutants is comparable to repression by tetrameric LacR when both auxiliary operators are not present. For a general review, see, Muller-Hill B. $Curr$ $Opin$ $Microbiol.$ 1(2): 145–51, 1998.

Ideal promoter systems for overproducing recombinant proteins in $E.$ $coli$ should: (1) provide strong expression of cloned genes; (2) function only under inducing conditions; and (3) have a simple method of induction so that large-scale operation is possible. However, while the available repertoire of $E.$ $coli$ expression systems usually produce high levels of the corresponding cloned gene products, in many cases synthesize substantial levels of cloned gene products in uninduced or repressed conditions. Generally, these systems include controllable expression vectors based on the strong inducible promoter, tac and T7. Both promoter systems have only one lac operon site to regulate the target gene expression. Full repression of these two strong promoters has been difficult to achieve. Furthermore, the leaky basal expression of some toxic proteins can have a detrimental impact on cell growth and viability.

Despite advances in the expression of recombinant proteins in bacterial hosts, there exists a need for improved methods for higher yields for protein production.

SUMMARY OF THE INVENTION

The present invention provides two novel $E.$ $coli$ synthetic promoters, Syn 1 (SEQ ID NO:1) and Syn 2 (SEQ ID NO:2). Syn 1 and Syn 2 are two tight regulated synthetic promoters that control uninduced, leaky expression of proteins that are toxic and interfere with production of recombinant protein from an $E.$ $coli$ expression system. Thus, these promoters provide an advantage by controlling basal expression of target genes. Specifically, these promoters provide a sterically repressed promoter in which an additional lac operator site is inserted between the –10 and –35 elements, where it can interfere sterically with binding of RNA Polymerase and thereby prevent the assembly of a poised transcriptional complex.

DESCRIPTION OF THE INVENTION

The most common biotechnological use of a promoter is to direct synthesis of a heterologous protein. However, a strong promoter is not necessarily optimal. The ability to turn the promoter off is as important as the promoter's strength. Promoters that are constitutively "on" are not generally used for protein expression in $E.$ $coli$ because of difficulties in the creation and maintenance of the plasmid construct. Two important reasons for this are that (i) production of heterologous protein in high yield is very draining to the resources of the cell, and (ii) many genes encode "toxic proteins". These factors can result in a strong selection against cells carrying such plasmid constructs and may be the cause of plasmid instability or even the inability to transform cells successfully. The strongest promoters may result in the accumulation of heterologous protein to more than 50% of the total cell protein. This reduces the cell's ability to produce proteins needed for growth. The phenomenon of foreign proteins' toxicity is well known, even though it is still poorly understood. Some general rules have been established, however, that can help predict the toxicity of given proteins. As an example, DNA-binding proteins tend to be highly toxic when overexpressed in $E.$ $coli$, as are proteins that disrupt vital functions such as electron transport or membrane integrity. These two factors, toxicity and the draining of cell resources, tend to select against cells carrying plasmids with genes expressed constitutively from strong promoters. To get around this problem, an inducible promoter is typically used to produce recombinant protein in E. coli. Such promoters remain off until a specific signal is delivered to the cell. Under control of this signal, the promoter is turned on only when the expression of the gene is desired. See e.g. Goldstein MA, Doi RH. Prokaryotic promoters in biotechnology. Biotechnol Annu Rev. 1995; 1: 105–28; see also Joseph M. Fernandez, James Hoeffler Gene Expression Systems: Using Nature for the Art of Expression, Published by Academic Press (January 1999) pgs. 45–64.

In 1982, de Boer and his colleagues reported the development of a hybrid trp/lac promoter. They showed that the −35 region of trp promoter in combination with the −10 region of lac promoter, separated by a 16-base pair spacing, resulted in a promoter stronger than either promoter alone. They designated this hybrid promoter system as the tac promoter. See e.g. de Boer H A, Comstock L J, Vasser M., "The tac promoter: a functional hybrid derived from the trp and lac promoters" Proc. Natl. Acad. Sci. 80(1): 21–5 (1983); see also U.S. Pat. No. 4,551,433; see also Amann E, Brosius J, Ptashne M, "Vectors bearing a hybrid trp-lac promoter useful for regulated expression of cloned genes in Escherichia coli" Gene 25(2–3): 167–78 (1983). However, all known inducible promoter systems have a residual level of activity or "leakiness" which leads to the inappropriate transcription and expression of the gene being cloned under the control of the promoter. In most cases, this is not a problem because the gene product being produced is well tolerated by the cell, i.e., the gene product is non-toxic. However, in instances where the gene product being produced is toxic or even lethal to the cell, even these small amounts of expression can be detrimental. In fact, there are certain toxic genes that have been characterized as "unclonable" because they are unstable in any cloning vector.

The present invention addresses and overcomes the problem of promoter leakiness by providing two novel E. coli synthetic promoters, Syn 1 (SEQ ID NO:1) and Syn 2 (SEQ ID NO:2). The present invention is further described below. However, the following definitions are provided to facilitate understanding of the invention.

As used herein, the term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., EMBO J. 4:1075 (1985); Nilsson et al., Methods EnzymoL 198:3 (1991)), glutathione S transferase (Smith and Johnson, Gene 67:31 (1988)). Glu-Glu affinity tag (Grussenrmeyer et al., Proc. Natl. Acad. Sci. USA 82:7952 (1985)), substance P, FLAG peptide (Hopp et al., Biotechnology 6:1204 (1988)), streptavidin binding peptide, or other antigenic epitope or binding domain. See, in general, Ford et al., Protein Expression and Purification 2;95 (1991). DNA molecules encoding affinity tags are available from commercial suppliers (e.g.. Pharmacia Biotech, Piscataway, N.J.).

The terms "amino-terminal" or "N-terminal" and "carboxyl-terminal" or "C-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "ARS" refers to a yeast autonomous replicating sequence.

The term "CEN6" refers to a yeast centromeric sequence.

A "cloning vector" is a nucleic acid molecule, such as a plasmid, cosmid, or bacteriophage, which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide resistance to antibiotic.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

The term "complement of a nucleic acid molecule" refers to a nucleic acid molecule having a complementary nucleotide sequence and reverse orientation as compared to a reference nucleotide sequence.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

A "core promoter" contains essential nucleotide sequences for promoter function, including the start of transcription. By this definition, a core promoter may or may not have detectable activity in the absence of specific sequences that may enhance the activity or confer tissue specific activity.

An "enhancer" is a type of regulatory element that can increase the efficiency of transcription, regardless of the distance or orientation of the enhancer relative to the start site of transcription.

The term "expression" refers to the biosynthesis of a gene product. For example, in the case of a structural gene, expression involves transcription of the structural gene into mRNA and the translation of mRNA into one or more polypeptides.

An "expression vector" is a nucleic acid molecule encoding a gene that is expressed in a host cell. Typically, an expression vector comprises a transcriptional promoter, a gene, an origin of replication, a selectable marker, and a transcriptional terminator. Gene expression is usually placed under the control of a promoter, and such a gene is said to be "operably linked to" the promoter. Similarly, a regulatory element and a core promoter are operably linked if the regulatory element modulates the activity of the core promoter. An expression vector may also be known as an expression construct.

A "fusion protein" is a hybrid protein expressed by a nucleic acid molecule comprising nucleotide sequences of at least two genes.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "heterologous" peptide or polypeptide means a peptide or polypeptide encoded by a non-host DNA molecule.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

"Linear DNA" denotes non-circular DNA molecules with free 5' and 3' ends. Linear DNA can be prepared from closed circular DNA molecules, such as plasmids, by enzymatic digestion or physical disruption.

"Nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or, more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally occurring or modified nucleic acid bases attached to a polyamide backbone. Nucleic acids can be either single stranded or double stranded.

A "polypeptide" is a polymer of amino acid residues joined by peptide bonds, whether produced naturally or synthetically. Polypeptides of less than about 10 amino acid residues are commonly referred to as "peptides."

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoters include, for example, but are not limited to, IPTG-inducible promoters, bacteriophage T7 promoters and bacteriophage $\lambda p_L$. Sea e.g. Smabrook et al., Molecular Cloning: A Laboratory Manual, 3rd ed., Cold Spring Harbor Laboratory Press, Cold Spring Harbor. N.Y. (2001). A typical prokaryotic promoter will have three components, consisting of consensus sequences at −35 and −10 with a sequence of between 16 and 19 nucleotides between them. See e.g. Lisset, S. and Margalit. H., Nucleic Acids Res. 21:1512 (1993). Promoters of this sort include the lac, trp, trp-lac (tac) and trp-lac(trc) promoters. If a promoter is an inducible promoter, then the rate of transcription increases in response to an inducing agent. In contrast, the rate of transcription is not regulated by an inducing agent if the promoter is a constinuive promoter. Repressible promoters are also known.

A "protein" is a macromolecule comprising one or more polypeptide chains. A protein may also comprise non-peptidic components, such as carbohydrate groups. Carbohydrates and other non-peptidic substituents may be added to a protein. Proteins are defined herein in terms of their amino acid backbone structures; substituents such as carbohydrate groups and non-peptidic groups are generally not specified, but may be present nonetheless.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The term "RBS II" refers to a synthetic ribosomal binding site sequence.

A "recombinant host" is a cell that contains a heterologous nucleic acid molecule, such as a cloning vector or expression vector.

A "regulatory element" is a nucleotide sequence that modulates the activity of a core promoter. For example, a eukaryotic regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner. Bacterial promoters have regulatory elements that bind and modulate the activity of the core promoter, such as operator sequences that bind activator or repressor molecules.

The term "RNAP" refers to RNA polymerase.

The term "rrnB" refers to an E. coli ribosomal RNA operon.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "tac promoter" refers to the hybrid *E. coli* promoter which contains the −10 region of the lac UV5 promoter and the −35 region of the trp promoter.

The term "URA3" refers to the yeast orotidine-5'-phosphate decarboxylase gene.

Due to the imprecision of standard analytical methods, molecular weights and lengths of polymers are understood to be approximate values. When such a value is expressed as "about" X or "approximately" X, the stated value of X will be understood to be accurate to ±10%.

Design of Syn 1 and Syn 2

The present invention addressed the need for preventing leaky expression of toxic genes in an *E. coli* expression system. The present invention is based on mechanistic information about the functioning of the lac promoter. This information was used to design a new promoter with a surprisingly improved efficiency of the repression of expression of toxic genes in an expression system. This high level of repression can be utilized to reduce or remove overproduction of toxic proteins in *E. coli*.

The tac promoter system has a lac operator centered at +13 with respect to the transcriptional start site. Binding of the lac repressor to the operator blocks transcriptional elongation. However, this interaction does not prevent the formation of a transcriptionally competent complex. In vitro footprinting and cross-linking studies demonstrated that the lac repressor and RNAP could occupy the promoter/operator region simultaneously. This may contribute to inadequate repression of promoter activity. See e.g. Straney S B, Crothers D M., "Lac repressor is a transient gene-activating protein" Cell. 1987 Dec. 4; 51(5): 699–707; see also Lee J, Goldfarb A. "Lac repressor acts by modifying the initial transcribing complex so that it cannot leave the promoter" Cell. 1991 Aug. 23; 66(4): 793–8; see also Mosrin-Huaman, C. "Translocation of *Escherichia coli* RNA polymerase against a protein roadblock in vivo highlights a passive sliding mechanism for transcript elongation" Mol Microbiol. 2004 Mar.;51(5):1471–81.

The present invention overcomes this problem by the addition of a second lac operator at a site where binding of the lac repressor would sterically block access of RNAP to the promoter. Syn 1 was constructed with two lac operator sites, one in the original location found in the tac promoter and the other located between the −10 and −35 sites. The expression vector containing Syn 1 promoter was derived from the expression vector containing the tac promoter, pTAP237, and was named pTAP399 (described in Example 2 below).

An attempt was made to improve the properties of Syn 1 by increasing its strength. The A+T rich region upstream of −40 in the rRNA rrnB P1 promoter, the UP element is known to increase transcription 30- to 70- fold by binding RNAP. See e.g. Estrem ST, "Identification of an UP element consensus sequence for bacterial promoters" Proc. Natl. Acad. Sci. 95(17):9761–6 (1998). Similar A+T rich sequences have been identified upstream of many bacterial and phage promoters, but they are not as highly conserved as −10 and −35 elements. A consensus UP element sequence was generated by selection in vitro for upstream sequences that promote rapid RNAP binding to rrnB P1 promoter, followed by an in vivo screen for high promoter activity. The consensus UP element consists of alternating A- and T-tracts. Gourse and colleagues found that the effects of UP elements on transcription correlated generally with the degree of similarity to the UP element consensus sequence. Id; see also Ross W., "*Escherichia coil* promoters with UP elements of different strengths: modular structure of bacterial promoters" J. Bacteriol. 180(20):5375–83 (1998). Thus. Syn 2 was constructed with two lac operator sites, as in Syn 1. However, Syn 2 conlains the UP element in the rRNA rrnB P1 promoter. The expression vector containing Syn 2 promoter was derived from the expression vector containing Syn 1, pTAP399, and was named pTAP413 (described in Example 3 below).

Accordingly, the present invention is based on two novel promoters, Syn 1 and Syn 2, both of which contain an additional lac operator between the −10 and −35 elements of the tac promoter. Syn 2 also has an UP element from the rrnB P1. The use of these two novel promoters resulted in more efficient repressed transcription without affecting the expression level of a gene after induction. Syn 2, as compared with Syn 1 has no additional impact on promoter strength, but does have a further increased efficiency of repression.

Expression Vectors

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

Selectable Marker Genes

A wide variety of selectable marker genes are available (see, for example, Kaufman, *Meth. Enzymol.* 185:487 (1990); Kaufman, *Meth. Enzymol.* 185:537 (1990)). In the present context, a suitable selectable marker is "titratable," in that the resistance of a cell to a high dose of toxic drug will be related to the number of selectable marker proteins produced by the cell. This characteristic is lacking when the selectable marker is an enzyme that can neutralize a high number of toxic drug molecules per enzyme.

As one skilled in the art would know selectable markers for bacterial expression include markers that confer antibiotic resistance. Antibiotics such as ampicillin, tetracycline, chloramphenicol, and kanamycin are commonly used. An expression vector can carry more than one such antibiotic resistance gene. See also, Sambrook et al., ibid. Other selectable markers can be used, as well, and in some cases it may be preferable to make use of a selectable marker that does not require the use of an antibiotic. One example of this sort of selectable marker uses the hok/sok system from plasmid R1. The hok gene encodes the toxic Hok protein of 52 amino acids and the sok gene encodes an antisense RNA, which is complementary to the hok mRNA leader sequence. This selectable marker is known to one skilled in the art and is described in more detail by Gerdes, K. et al., *Genetic Engineering*, 19:49–61, 1997.

Suitable *E. coli* Hosts

Suitable prokaryotic hosts include *E. coli* strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). However, suitable hosts are not limited to these strains.

Bacterial Expression

When expressing a polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)). Standard methods for introducing expression vectors into bacterial cells are provided, for example, by Ausubel (1995).

The invention is further illustrated by the following non-limiting examples.

EXAMPLE 1

Construction of Plasmid pTAP237

Plasmid pTAP237 was generated by inserting a PCR-generated linker into the SmaI site of pTAP186 by homologous recombination. Plasmid pTAP186 was derived from the plasmids pRS316 (a *Saccharomyces cerevisiae* shuttle vector) and pMAL-c2, an *E. coli* expression plasmid derived from pKK223-3 and comprising the tac promoter and the rrnB terminator. Plasmid pTAP186 contains a kanamycin resistance gene in which the Sma I site has been destroyed and has NotI and SfiI sites flanking the yeast ARS-CEN6 and URA3 sequences, facilitating their removal from the plasmid by digestion with NotI. The PCR-generated linker replaced the expression coupler sequence in pTAP186 with the synthetic RBS II sequence. It was prepared from 100 pmoles each of oligonucleotides zc29,740 (SEQ ID NO: 3) and zc29,741 (SEQ ID NO: 4), and approximately 5 pmoles each of oligonucleotides zc29,736 (SEQ ID NO: 5) and zc29,738 (SEQ ID NO: 6). These oligonucleotides were combined by PCR for ten cycles of 94° C. for 30 seconds, 50° C. for 30 seconds, and 72° C. for 30 seconds, followed by 4° C. soak. The resulting PCR products were concentrated by precipitation with two times the volume of 100% ethanol. The pellet was resuspended in 10 μL water to be used for recombining into the recipient vector pTAP186 digested with SmaI to produce the construct containing the synthetic RBS II sequence. Approximately 1 μg of the PCR-generated linker and 100 ng of pTAP186 digested with SmaI were mixed together and transformed into competent yeast cells (*S. cerevisiae* SF838-9Dα). The yeast was then plated onto −URA DS plates and left at room temperature for about 72 hours.

The Ura+ yeast transformants from a single plate were resuspended in 2–3 ml H$_2$O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 500 μl phenol-chloroform and vortexed for 1 minute. The mixture was then spun for 5 minutes in an Eppendorf centrifuge at maximum speed. Three hundred microliters of the aqueous phase was transferred to a fresh tube, and the DNA precipitated with 600 μl 100% ethanol, followed by centrifugation for 10 minutes at 4° C. The DNA pellet was resuspended in 100 μl H$_2$O.

One microliter of the recovered DNA was transformed into *E. coli* MC1061. Clones were screened by colony PCR as disclosed above but using 25 cylces and using 20 pmoles each of oligonucleotide zc29,740 (SEQ ID NO: 3) and zc29,741 (SEQ ID NO: 4). Clones displaying the correct size band on an agarose gel were subject to sequence analysis. The correct plasmid was designated pTAP237.

EXAMPLE 2

Construction of Plasmid pTAP399 Containing Syn 1

The plasmid pTAP399 was derived from pTAP237 (described in Example 1). The objective of this study was to use mechanistic information about the functioning of the lac promoter to design a new promoter with improved efficiency of repression, which could be employed in overproduction of toxic proteins in *E. coli*. The tac promoter system has a lac operator centered at +13 with respect to the transcriptional start site. Binding of the lac repressor to the operator blocks transcriptional elongation. However, this interaction does not prevent the formation of a transcriptionally competent complex. In vitro footprinting and cross-linking studies demonstrated that the lac repressor and RNAP could occupy the promoter/operator region simultaneously. This may contribute to inadequate repression of promoter activity.[12, 13, 14, 15, 16] In an attempt to circumvent this problem, we decided to add an additional lac operator at a site where binding of the lac repressor would sterically block access of RNAP to the promoter. This design was inspired by the mechanism that regulates the lambda pL and recA promoters. Syn 1, was constructed with two lac operator sites, one in the original location found in the tac promoter and the other located between the −10 and −35 sites. The expression vector containing Syn 1 promoter was derived from the expression vector containing the tac promoter, pTAP237, and was named pTAP399.

Specifically, the PCR-generated linker replaced the tac promoter in pTAP237 (described in Example 1) with the synthetic promoter Syn 1 (SEQ ID NO:1). The Syn 1 promoter has two lac operator sites. One of lac operator is positioned between the consensus −10 and −35 element sequences, where it can interfere sterically with RNA polymerase and thereby prevent assembly of a poised transcriptional complex. The other lac operator site is inserted 10 bp downstream from the novel promoter, where can block the initiation of mRNA synthesis. It was prepared from 100 pmoles each of oligonucleotide zc42,180 (SEQ ID NO:7) and zc42,167 (SEQ ID NO:8), and approximately 5 pmoles each of oligonucleotide zc42,181 (SEQ ID NO:9) and zc42,179 (SEQ ID NO:10). These oligonucleotides were combined by PCR for ten cycles of 94° C. for 30 seconds, 50° C. for 30 seconds, and 72° C. for 30 seconds, followed by 4° C. soak. The resulting PCR products were concentrated by precipitation with two times the volume of 100% ethanol. The pellet was resuspended in 10 µL water to be used for recombining into the recipient vector pTAP237 digested with BseRI to produce the construct containing the synthetic promoter (Syn 1) sequence. Approximately 1 µg of the PCR-generated linker and 100 ng of pTAP237 digested with BseR I were mixed together and transformed into competent SF838-9Dα yeast cells (*S. cerevisiae*). The yeast was then plated onto −URA DS plates and left at 30 C for about 72 hours.

The Ura+ yeast transformants from a single plate were resuspended in 2–3 ml H$_2$O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 µl acid washed glass beads and 500 µl phenol-chloroform and vortexed for 1 minute. The mixture was then spun for 5 minutes in an Eppendorf centrifuge at maximum speed. Three hundred microliters of the aqueous phase was transferred to a fresh tube, and the DNA precipitated with 600 µl 100% ethanol, followed by centrifugation for 10 minutes at 4° C. The DNA pellet was resuspended in 100 µl H$_2$O.

One microliter of the recovered DNA was transformed into *E. coli* MC1061. Clones were screened by colony PCR as disclosed above but using 25 cycles and using 20 pmoles each of oligonucleotide zc42,180 (SEQ ID NO:7) and zc42,167 (SEQ ID NO:8). Clones displaying the correct size band on an agarose gel were subject to sequence analysis. The correct plasmid was designated pTAP399 and was deposited with the American Type Culture Collection in Manassas, Va. and assigned ATCC Accession No. PTA-5700.

EXAMPLE 3

Construction of Plasmid pTAP413 Containing Syn 2

The plasmid pTAP413 was derived from pTAP399 (described in Example 2). The PCR-generated linker replaced the Syn1 (SEQ ID NO:1) promoter sequence in pTAP399 with the Syn 2 sequence (SEQ ID NO:2). The Syn 2 promoter contains two lac operons and shares similar basic structure as Syn 1 promoter. However, Syn 2 contains a 40 bp long DNA sequence that is located six bases upstream from −35 element. The sequence of the Syn 2 promoter in this region was derived from the UP element sequence of the rrnB1P1 promoter. It was prepared from 100 pmoles each of oligonucleotides zc42,734 (SEQ ID NO:11) and zc42,733 (SEQ ID NO:12), and approximately 5 pmoles each of oligonucleotides zc42,721 (SEQ ID NO:13) and zc42,718 (SEQ ID NO:14). These oligonucleotides were combined by PCR for ten cycles of 94° C. for 30 seconds, 50° C. for 30 seconds, and 72° C. for 30 seconds, followed by 4° C. soak. The resulting PCR products were concentrated by precipitation with two times the volume of 100% ethanol. Pellet was resuspended in 10 µL water to be used for recombining into the recipient vector pTAP399 digested with EcoRI to produce the construct containing the synthetic promoter Syn 2 (SEQ ID NO:2). Approximately 1 µg of the PCR-generated linker and 100 ng of pTAP399 digested with EcoRI were mixed together and transformed into competent SF8389Fα yeast cells (*S. cerevisiae*). The yeast was then plated onto −URA DS plates and left at room temperature for about 72 hours.

The Ura+ yeast transformants from a single plate were resuspended in 2–3 ml H$_2$O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 µl acid washed glass beads and 500 µl phenol-chloroform and vortexed for 1 minute. The mixture was then spun for 5 minutes in an Eppendorf centrifuge at maximum speed. Three hundred microliters of the aqueous phase was transferred to a fresh tube, and the DNA precipitated with 600 µl 100% ethanol, followed by centrifugation for 10 minutes at 4° C. The DNA pellet was resuspended in 100 µl H$_2$O.

One microliter of the recovered DNA was transformed into *E. coli* MC1061. Clones were screened by colony PCR as disclosed above but using 25 cycles and using 20 pmoles each of oligonucleotide zc42,733 (SEQ ID NO:12) and zc42,734 (SEQ ID NO:11). Clones displaying the correct size band on an agarose gel were subject to sequence analysis. The correct plasmid was designated pTAP413 and was deposited at the American Type Culture Collection in Manassas, Va. assigned ATCC Accession No. PTA-5701.

EXAMPLE 4

Construction of Plasmids-pTAP411, pTAP412 and pTAP414 Containing Different UP Element Sequences The plasmids pTAP411, pTAP412 and pTAP414 were all derived from pTAP399 (described in Example 2). The PCR-generated linker replaced the Syn1 (SEQ ID NO:1) promoter sequence in pTAP399 with the Syn 2 sequence (SEQ ID NO:2). Furthermore, PCR-generated linkers replaced the upstream sequence (from position −40 to −60) in pTAP399 with different UP element sequences from other sources. These linkers were prepared from different sets of partially overlapping oligonucleotides as follows:

A) pTAP411 pTAP411 contains a Syn 1 with an UP element consensus sequence (SEQ ID NO:24) and was prepared from 5 pmoles of oligonucleotides zc42718 (SEQ ID NO:14) and zc42719 (SEQ ID NO:15) and 100 pmoles of oligonucleotides zc42733 (SEQ ID NO:12) and zc42734 (SEQ ID NO:11).

B) pTAP412 pTAP412 contains a Syn 1 with rrnD P1 UP element sequence (SEQ ID NO:25) and was prepared from 5 pmoles of oligonucleotides zc42718 (SEQ ID NO:14) and zc42720 (SEQ ID NO:16) and 100 pmoles of oligonucleotides zc42733 (SEQ ID NO:12) and zc42734 (SEQ ID NO:11).

C) pTAP414 pTAP414 contains a Syn 1 with rrnB P2 UP element sequence (SEQ ID NO:26) and was prepared from 5 pmoles of oligonucleotides zc42718 (SEQ ID NO:14) and zc42727 (SEQ ID NO:17) and 100 pmoles of oligonucleotides zc42733 (SEQ ID NO:12) and zc42734 (SEQ ID NO:11).

The oligonucleotides in each set (as described above) were combined by PCR in ten cycles of 94° C. for 30 seconds, 50° C. for 30 seconds, and 72° C. for 30 seconds, followed by 4° C. soak. The resulting PCR products were concentrated by precipitation with two times the volume of 100% ethanol. The pellet was resuspended in 10 μL H₂O and used for recombination into the recipient vector, pTAP399, digested with BseRI to produce constructs containing the Syn 1 promoter sequence coupled with appropriate UP element. Approximately 1 μg of the PCR-generated linker and 100 ng of pTAP399 digested with BseRI were mixed together and transformed into competent yeast cells (*S. cerevisiae*). The cells were then plated onto −URA DS plates and left at room temperature for about 72 hours.

The Ura+ yeast transformants from a single plate were resuspended in 2–3 ml H₂O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 500 μl phenol-chloroform and vortexed for 1 minute. The mixture was then spun for 5 minutes in an Eppendorf centrifuge at maximum speed. Three hundred microliters of the aqueous phase was transferred to a fresh tube, and the DNA precipitated with 600 μl 100% ethanol, followed by centrifugation for 10 minutes at 4° C. The DNA pellet was resuspended in 100 μl H₂O.

One microliter of the recovered DNA was transformed into *E. coli* MC1061. DNA was recovered and transformed into *E. coli* MC1061. Clones were screened by colony PCR using the reaction conditions described above but using 25 cycles and 20 pmoles each of oligonucleotides zc42,180 and zc42,167. Clones displaying a band of the correct size on an agarose gel were subjected to DNA sequence analysis. The resulting plasmids were designated pTAP411 (Syn 1 with UP element consensus sequence), pTAP412 (Syn 1 with rrnD P1 UP element sequence) and pTAP414 (Syn 1 with rrnB P2 UP element sequence).

EXAMPLE 5

Construction of Expression Constructs Containing Human IL-20 and Comparison of Promoter Strength A series of plasmids was constructed to express the human IL-20 (SEQ ID NO: 18; amino acid sequence SEQ ID NO:19) which was codon optimized for *E. coli*. A DNA fragment of human IL-20 was isolated using PCR with two primers, primer zc29,957 (SEQ ID NO:20) and primer zc23,993 (SEQ ID NO:21). Primer zc29,957 (SEQ ID NO:20) contained 41 bp of flanking vector sequence and 24 bp corresponding to the amino terminus of human IL-20 (SEQ ID NO:18). Primer zc23,993 (SEQ ID NO:21) contained 38 bp corresponding to the 3' end of the vector which contained the human IL-20 insert. The PCR conditions were as follows: 25 cycles at 94° C. for 30 seconds, 50° C. for 30 seconds, and 72° C. for 1 minute; followed by a 4° C. soak. A small aliquot (2–4 μL) of the PCR sample was run on a 1% agarose gel with 1× TBE buffer for analysis and the expected 500 bp fragment was observed. The remaining volume of the 100 μL reaction was precipitated with 200 μL absolute ethanol. Pellet was resuspended in 10 μL H₂O and used for recombination into SmaI cut recipient the six vectors, as described in Examples 1–4 above, to produce the constructs encoding human IL-20.

All six constructs were then cut with NotI restriction enzyme (New England Biolabs) to remove the yeast sequence from the vector backbone, thus streamlining the vector. Ten microliters plasmid DNA was incubated with 15 μl H₂O, 3 μl buffer 3 (NEB) and 2.0 μl NotI enzyme at 37° C. for one hour. The reaction was then immediately religated. Seven microliters of the restriction digest was incubated with 2 μl of 5× buffer and 1 μl of ligase for 30 minutes at room temperature. One microliter of the ligation reaction was transformed into *E. coli*. The transformed bacteria were selected for by plating on LB agar containing appropriate antibiotic.

Two colonies from each ligation reaction were selected from the transformation plates and grown overnight in LB plus appropriate antibiotic. Plasmid DNA was prepared using QIAprep Spin Miniprep Kit (Qiagen). Aliquots of the DNA were digested with PvuII and PstI to confirm the absence of the yeast sequence. Individual clones harboring the correct expression construct for the human IL-20 were identified by restriction digest to verify the presence of the human IL-20 insert. The resulting clones were designated as pTAP255 (derived from pTAP237) pTAP407 (derived from pTAP399), pTAP426, (derived from pTAP411), pTAP427 (derived from pTAP412), pTAP428 (derived from pTAP413) and pTAP429 (derived from pTAP414). The Not I digested plasmids were re-ligated and transformed into *E. coli* host strain W3110.

Transformation of electrocompetent *E. coli* W3110 cells was done with 1 μl ligated plasmid DNA and 50 μl of W3110 cells (competent cells were made in-house). The cells were electropulsed in 0.1 cm cuvettes at 1.75 kV, 25 μF and 100 Ω. Following electroporation, 250 μl SOC (2% Bacto Tryptone (Difco, Detroit, Mich.), 0.5% yeast extract (Difco), 10 mM NaCl, 2.5 mM KCl, 10 mM MgCl₂, 10 mM MgSO₄, 20 mM glucose) was added to each sample and outgrown at 37° C. for 1 hour. The entire 250 μl sample was plated in one aliquot on an LB kanamycin plate [LB broth (Lennox), 1.8% Bacto Agar (Difco), 25 mg/L kanamycin (Sigma)]. Plates were incubated at 37° C. overnight. Six clones for each construct were picked for follow-up analysis. They were grown in 2.0 ml Superbroth II (Becton Dickinson) containing 25 μg/ml kanamycin at 37° C. overnight. The following day, 1.0 ml of the overnight digest was used to confirm presence of plasmid DNA. The Qiagen Spin Miniprep Kit (Qiagen) was used to make plasmid DNA, following manufacturer's instructions. 1 μl of DNA was digested with EcoRI (Gibco BRL)/NotI (New England Biolabs) to verify the correct plasmid restriction digest pattern.

Induction of cells were done as follows. 37.5 ml of Superbroth 2+kan 30 μg/ml were inoculated with 375 μl of starter culture. Cultures grew at 37 C for 1 hour and 50 minutes. They were then induced with 1 mM IPTG. 12.5 ml of culture was grown at 37 C and 12.5 ml was grown at 30 C of the expressed protein at lower temperature. 12.5 mls was not induced for a control. Cultures were harvested at 3 hours post-induction. 250 μl of culture was mixed with 250 μl glass beads and 250 μl of Thorner Buffer/5% dye/5% βME. Samples were vortexed, then boiled for 5 minutes, and run on a PAGE gel. 20 μl were loaded per lane on a 4–12% NuPAGE Bis-Tris gel (NOVEX). Gels were run in 1×MES buffer.

EXAMPLE 6

Comparison of Gene Expression Between the Syn 1 and tac Promoters

In order to compare the strength of gene expression between the promoters of the present invention, the expression level of human IL-20 was used to compare gene expression driven by the Syn 1 and the tac promoter. pTAP237 and pTAP399 are closely related in structure except in their promoter region; hence, differences in the expression of IL-20 should be attributable to differences in promoter activity. Mature human IL-20 coding sequence (SEQ ID NO:18) was subcloned into pTAP237 and pTAP399, creating constructs pTAP255 and pTAP407, respectively (described above). The expression level of IL-20 after IPTG induction in E. coli transformed with either vector was then compared. The amount of human IL-20 present in a lysate from a culture harboring pTAP407 (pTAP399/hIL-20) is similar to that observed in an extract from a culture harboring pTAP255 (pTAP237/hIL-20). This demonstrates that these two promoters have comparable strength, suggesting that insertion of an additional lac operator between the −35 and −10 regions of the tac promoter has no negative impact on the promoter strength.

EXAMPLE 7

Basal Expression of Human IL-20 Using tac, Syn 1, Syn 2 and Other Sterically Repressed Promoters in E. coli Numerous studies have indicated that the tac promoter is leaky. A substantial level of IL-20 was produced in the absence of induction with IPTG. To address differences in pre-induction leakage, the expression levels of human IL-20, controlled by the tac and srp promoters, were compared by Western blot analysis using an anti-IL20 monoclonal antibody as the probe. Thus, a NuPAGE 4–12% Bis Tris gel (Invitrogen) was run using 1×MES buffer. 2.5 μl of uninduced culture was loaded per lane (5 μl of culture and buffer). A human IL-20 standard (designated A309F) was loaded as 25 ng and 50 ng. After the gel was run, the DNA was transferred to a nitrocellulose membrane via a Novex transfer box and protocol. The membrane was then blocked in 5% milk and TBBS (160 mM NaCl, 0.1% Tween 20, 20 mM Tris pH7.4) for 30 minutes. It was then incubated at room temperature with an anti-human IL-20 monoclonal antibody (designated E0582) as a 1:5000 dilution. The blot was then washed twice in TTBS for 5–10 minutes each. The washed blot was incubated at room temperature for one hour in a 1:5000 dilution of goat anti-mouse antibody (Bio-Rad Laboratories, Hercules, Calif.). The blot was then washed again in TTBS under the same conditions. The washed blot was then exposed to ECL reagent (Amersham) and exposed to film.

The amount of human IL-20 present in a lysate from a culture harboring pTAP407 (pTAP399/Syn 1/hIL-20) is approximately five-fold lower than that observed in a lysate from a culture harboring pTAP255 (pTAP237/tac/hIL-20). The results confirmed that tac promoter was leaky and produced substantial levels of IL-20 in uninduced conditions. Syn 1 promoter was capable to reduced the IL-20 leaky expression by 80%.

Syn 1 was altered in an attempt to improve its strength by inserting different UP elements upstream of the promoter region. We compared the effects of the UP elements on the expression of IL-20 in E. coli after IPTG induction. The amounts of IL-20 present in lysates from cultures harboring expression constructs with different UP element sequences were comparable to that observed in a lysate from a culture harboring pTAP407 (pTAP399/hIL-20), which lacks an UP element. This result demonstrates that addition of different UP element sequences to Syn 1 had no impact on the promoter strength. However, the expression level of IL-20 under uninduced conditions was also examined. It was discovered that different UP element sequences had different impacts on basal expression of IL-20. Most strikingly, it was observed that Syn 2, which contains the rrnB P1 UP element, was able to suppress the basal expression of IL-20 to a level that could not be detected by Western blotting techniques.

EXAMPLE 8

Evaluation of Pre-Induction Leakage of Syn 1 and Syn 2 in DNaseI Expression Vectors To test pre-induction leakage of the promoters of the present invention, a gene coding for a protein known to be toxic to E. coli, DnaseI, was cloned into pTAP237, pTAP399 and pTAP413. A DNA fragment of human DNaseI was isolated using PCR with two primers, primer zc47,073 (SEQ ID NO:22) and primer zc47,074 (SEQ ID NO:23). Primer zc47,073 contained 41 bp of flanking vector sequence and 24 bp corresponding to the amino terminus of human DNaseI. Primer zc47,074 contained 38 bp corresponding to the 3' end of the vector which contained the human DNaseI insert. The PCR conditions were as follows: 30 cycles at 94° C. for 1 min, 50° C. for 1 min, and 72° C. for 1 minute; followed by a 4° C. soak. A small aliquot (2–4 μL) of the PCR sample was run on a 1% agarose gel with 1× TBE buffer for analysis and the expected 500 bp fragment was observed. The remaining volume of the 100 μL reaction was precipitated with 200 μL absolute ethanol. Approximately 1 μg of the PCR product and 100 ng of SmaI cut recipient vectors (pTAP237, pTAP399 and pTAP413) were mixed together and transformed into competent SF8389Dα yeast cells (S. cerevisiae). The cells were then plated onto −URA DS plates and left at room temperature for about 72 hours.

The Ura+ yeast transformants from a single plate were resuspended in 2–3 ml H$_2$O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 500 μl phenol-chloroform and vortexed for 1 minute. The mixture was then spun for 5 minutes in an Eppendorf centrifuge at maximum speed. Three hundred microliters of the aqueous phase was transferred to a fresh tube, and the DNA precipitated with 600 μl 100% ethanol, followed by centrifugation for 10 minutes at 4° C. The DNA pellet was resuspended in 100 μl H$_2$O.

One microliter of the recovered DNA was transformed into E. coli DH10B. As expected, the tac-controlled DNaseI expression construct could not be established in E. coli host DH10B. In contrast, viable clones could be established with both of the Syn 1 and Syn 2-controlled vectors. Induction of DNaseI expression in the resulting clones led to cell clumping and lysis in liquid culture, indicating that active DNase was expressed after IPTG induction and demonstrating the utility of both Syn 1 and Syn 2 for production of toxic genes in E. coli.

EXAMPLE 9

Evaluation of Pre-Induction Leakage of Syn 1 and Syn 2 in T7 Bacteriophage 0.7 Gene Expression Vectors To test pre-induction leakage of the promoters of the present invention, a gene coding for a protein known to be toxic to E. coli, the 0.7 gene, was cloned into promoters of the present invention. The full length 0.7 gene was subcloned into pTAP237 (under the control of tac promoter), pTAP399 (under the control of Syn 1 promoter) and pTAP413 (under the Syn 2 promoter). The 0.7 gene was isolated using PCR with two primers, primer zc48069 (SEQ ID NO:27) and primer zc48070 (SEQ ID NO:28). Primer zc48069 contained 41 bp of flanking vector sequence and 24 bp corresponding to the amino terminus of T7 bacteriophage 0.7 gene (SEQ ID NO:29). Primer zc48070 contained 38 bp corresponding to the 3' end of the vector which contained the T7 bacteriophage 0.7 gene insert. The PCR conditions were as follows: 30 cycles at 94° C. for 1 min, 50° C. for 1 min, and 72° C. for 1 minute; followed by a 4° C. soak. A small aliquot (2–4 μL) of the PCR sample was run on a 1% agarose gel with 1× TBE buffer for analysis and the expected 1 kb fragment was observed. The remaining volume of the 100 μL reaction was precipitated with 200 μL absolute ethanol. Approximately 1 μg of the PCR product and 100 ng of SmaI cut recipient vectors pTAP237, pTAP399 and pTAP413 (described in Examples 1, 2 and 3) were mixed together and transformed into competent SF8389Dα yeast cells (*S. cerevisiae*). The cells were then plated onto −URA DS plates and left at room temperature for about 72 hours. The Ura+ yeast transformants from a single plate were resuspended in 2–3 ml $H_2O$ and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 500 μl phenol-chloroform and vortexed for 1 minute. The mixture was then spun for 5 minutes in an Eppendorf centrifuge at, maximum speed. Three hundred microliters of the aqueous phase was transferred to a fresh tube, and the DNA precipitated with 600 μl ethanol, followed by centrifugation for 10 minutes at 4° C. The DNA pellet was resuspended in 100 μl $H_2O$.

One microliter of the recovered DNA was transformed into *E. coli* DH10B. Viable clones only could be established in *E. coli* host DH10B with the Syn 2-controlled vectors. It demonstrated that the Syn 2-controlled vector was able to reduce the basal expression of 0.7 gene to levels that would permit isolation of stable recombinant plasmids.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. An isolated polynucleotide comprising SEQ ID NO: 1.
2. An isolated polynucleotide comprising the polynucleotide of claim 1 operably linked to a heterologous nucleic acid.
3. An isolated polynucleotide comprising SEQ ID NO: 2.
4. An isolated polynucleotide comprising the polynucleotide of claim 3 operably linked to a heterologous nucleic acid.
5. An expression vector comprising the polynucleotide of claim 2.
6. An expression vector comprising the polynucleotide of claim 4.
7. A host cell comprising the expression vector of claim 5.
8. The host cell of claim 7, wherein the host cell is stably transformed with the expression vector.
9. A host cell comprising the expression vector of claim 6.
10. The host cell of claim 9, wherein the host cell is stably transformed with the expression vector.

* * * * *